(12) United States Patent
Ewart et al.

(10) Patent No.: US 10,647,789 B2
(45) Date of Patent: May 12, 2020

(54) PROCESS FOR MAKING ETHYLENE-BASED POLYMERS USING CARBON-CARBON FREE RADICAL INITIATORS

(71) Applicant: Dow Global Technologies LLC, Midland, MI (US)

(72) Inventors: Sean Ewart, Freeport, TX (US); Teresa Karjala, Freeport, TX (US); Mehmet Demirors, Freeport, TX (US); Richard Keaton, Freeport, TX (US); Sarat Munjal, Freeport, TX (US); Christopher Eddy, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 108 days.

(21) Appl. No.: 15/736,196

(22) PCT Filed: Jun. 21, 2016

(86) PCT No.: PCT/US2016/038504
§ 371 (c)(1),
(2) Date: Dec. 13, 2017

(87) PCT Pub. No.: WO2016/209807
PCT Pub. Date: Dec. 29, 2016

(65) Prior Publication Data
US 2018/0171042 A1  Jun. 21, 2018

Related U.S. Application Data

(60) Provisional application No. 62/182,708, filed on Jun. 22, 2015.

(51) Int. Cl.
| | |
|---|---|
| *C08F 4/64* | (2006.01) |
| *C08F 4/76* | (2006.01) |
| *C08F 255/00* | (2006.01) |
| *C08F 10/02* | (2006.01) |
| *C08F 2/00* | (2006.01) |
| *C08F 2/34* | (2006.01) |
| *C08F 110/02* | (2006.01) |
| *C08F 210/02* | (2006.01) |
| *C07C 15/18* | (2006.01) |

(52) U.S. Cl.
CPC .............. *C08F 10/02* (2013.01); *C07C 15/18* (2013.01); *C08F 2/001* (2013.01); *C08F 2/34* (2013.01); *C08F 4/76* (2013.01); *C08F 110/02* (2013.01); *C08F 210/02* (2013.01)

(58) Field of Classification Search
CPC ...... C08F 2/001; C08F 255/00; C08F 255/02; C08F 255/04; C08F 255/08; C08F 255/10; C08F 4/64193
USPC ............................................. 526/65
See application file for complete search history.

(56) References Cited

U.S. PATENT DOCUMENTS

| | | | |
|---|---|---|---|
| 5,268,440 A * | 12/1993 | Luft | C08F 10/02 526/352.2 |
| 5,272,236 A | 12/1993 | Lai et al. | |
| 5,278,272 A | 1/1994 | Lai et al. | |
| 5,306,791 A * | 4/1994 | Muehlenbernd | C08F 10/02 526/86 |
| 5,844,045 A | 12/1998 | Kolthammer et al. | |
| 5,869,575 A | 2/1999 | Kolthammer et al. | |
| 6,448,341 B1 | 9/2002 | Kolthammer et al. | |
| 6,538,070 B1 | 3/2003 | Cardwell et al. | |
| 6,545,088 B1 | 4/2003 | Kolthammer et al. | |
| 6,566,446 B1 | 5/2003 | Parikh et al. | |
| 6,967,229 B2 | 11/2005 | Voorheis | |
| 8,247,696 B2 | 8/2012 | Smedberg et al. | |
| 8,372,931 B2 | 2/2013 | Hermel-Davidock et al. | |
| 9,045,628 B2 * | 6/2015 | Ewart | C08L 23/06 |
| 2005/0164872 A1 | 7/2005 | Boussie et al. | |
| 2006/0047049 A1 | 3/2006 | Onishi et al. | |
| 2010/0108357 A1 | 5/2010 | Smedberg et al. | |
| 2010/0168330 A1 * | 7/2010 | Demoirors | C08F 110/02 525/53 |
| 2010/0311927 A1 | 12/2010 | Karjala et al. | |
| 2011/0130533 A1 * | 6/2011 | Karjala | C08F 10/02 526/170 |
| 2013/0253126 A1 | 9/2013 | Ewart et al. | |
| 2013/0287985 A1 * | 10/2013 | Demirors | C08K 5/01 428/36.9 |

FOREIGN PATENT DOCUMENTS

| | | |
|---|---|---|
| EP | 0298432 A2 | 1/1989 |
| EP | 0313076 A2 | 4/1989 |
| WO | 2007/136494 A2 | 11/2007 |
| WO | 2009/114661 A1 | 9/2009 |

OTHER PUBLICATIONS

T. Williams et al., Polymer Letters, vol. 6, 1968, pp. 621-624.
G. Luft et al., Die Angewandte Makromolekulare Chemie 160 (1988), 193-201.
C. Ruchardt et al., Angew. Chem. Int. Ed. Engl. 19, 429-440 (1980).

* cited by examiner

*Primary Examiner* — Rip A Lee
(74) *Attorney, Agent, or Firm* — Quarles & Brady LLP (57) ABSTRACT

A composition comprising an ethylene-based polymer is made by a process comprising the steps of: (A) contacting under first polymerization conditions at least ethylene and at least one molecular catalyst to form a first ethylene-based polymer, and (B) contacting under second polymerization conditions the first ethylene-based polymer of (A) with at least additional ethylene and a carbon-carbon free radical initiator of Structure (I): wherein $R_1$, $R_2$, $R_3$, $R_4$, $R_5$ and $R_6$ are each, independently, hydrogen or a hydrocarbyl group and wherein, optionally, two or more R groups ($R_1$, $R_2$, $R_3$, $R_4$, $R_5$ and $R_6$) form a ring structure, with the proviso that at least one of $R_2$ and $R_5$, and at least one of $R_3$ and $R_6$ is a hydrocarbyl group of at least two carbon atoms, to form the composition.

12 Claims, 2 Drawing Sheets

PROCESS FOR MAKING ETHYLENE-BASED POLYMERS USING CARBON-CARBON FREE RADICAL INITIATORS

REFERENCE TO RELATED APPLICATIONS

The present application claims the benefit of U.S. Provisional Application 62/182,708, filed Jun. 22, 2015.

BACKGROUND OF THE INVENTION

As described in patent documents WO 2010/141557, US 2011/0130533 and WO 2012/074812, ethylene-based copolymers can be produced by simultaneously producing high density polyethylene or linear low density polyethylene and low density polyethylene in a high pressure reactor. The high density polyethylene is produced in a first reactor or reactor zone in the presence of a molecular catalyst and the low density polyethylene is produced in a second reactor or reactor zone using a free radical initiator. The free radical initiators used previously for this work are typical peroxide initiators which contain polar functionalities. These peroxides decompose to make polar byproducts which are known to deactivate the molecular catalysts resulting in unstable operation and reduced catalyst efficiency, particularly in those processes in which unreacted ethylene and/or polar byproducts from the second reactor zone is recycled to the first reactor zone. Aluminum alkyls can be used to scavenge the polar byproducts and prevent them from deactivating the molecular catalysts, however use of these aluminum alkyls is both economically disadvantageous and can lead to undesired chain transfer reactions.

In one embodiment of this invention, hydrocarbon free radical initiators are used in lieu of peroxide free radical initiators so as to avoid the formation of polar byproducts. Decomposed hydrocarbon free radical initiators have less detrimental impact on the activity and life of molecular catalysts, and this is particularly important in those embodiments in which unreacted ethylene and/or polar byproducts are recycled from the second reaction zone to the first reaction zone. The combination of molecular catalysts with hydrocarbon based free radical initiators can be used to produce interconnected ethylene copolymers with improved catalyst efficiencies and reduced aluminum alkyl requirements. Another advantage of using hydrocarbon based initiators is that the interconnected ethylene copolymer can be produced in a single reactor or reaction zone without having to physically separate the two reaction zones.

SUMMARY OF THE INVENTION

In one embodiment, the invention is a process for making a composition comprising an ethylene-based polymer, the process comprising the steps of:
(A) contacting under first polymerization conditions at least ethylene and at least one molecular catalyst to form a first ethylene-based polymer, and
(B) contacting under second polymerization conditions the first ethylene-based polymer of (A) with at least additional ethylene and a carbon-carbon free radical initiator of Structure I:

(Structure I)

wherein $R_1$, $R_2$, $R_3$, $R_4$, $R_5$ and $R_6$ are each, independently, hydrogen or a hydrocarbyl group and wherein, optionally, two or more R groups ($R_1$, $R_2$, $R_3$, $R_4$, $R_5$ and $R_6$) form a ring structure, with the proviso that at least one of $R_2$ and $R_5$, and at least one of $R_3$ and $R_6$ is a hydrocarbyl group of at least two carbon atoms, to form a polymer composition comprising a second ethylene-based polymer.

In one embodiment the invention is an ethylene-based polymer made by the process of this invention.

In one embodiment the invention is a composition comprising an ethylene-based polymer made by the process of this invention.

DETAILED DESCRIPTION OF THE PREFERRED EMBODIMENT

An inventive process may comprise a combination of two or more embodiments as described herein.

In one embodiment, the second ethylene-based polymer is polymerized in the presence of a free radical initiator.

In one embodiment, the first ethylene-based polymer and the second ethylene-based polymer are polymerized simultaneously.

In one embodiment, the process takes place in one reaction zone.

In one embodiment, the process takes place in at least two reaction zones.

In one embodiment, the first polymerization conditions are the same as the second polymerization conditions.

In one embodiment, the second polymerization conditions differ from the first polymerization conditions in one or more features, such as molecular catalyst concentration, Structure I concentration, polymerization temperature and/or polymerization pressure.

In one embodiment, the second ethylene-based polymer differs from the first ethylene-based polymer in one or more of the following features Mn, Mw, MWD, melt index (I2), density, and/or Tm (melting temperature).

In one embodiment, the first ethylene-based polymer is polymerized first, and the second ethylene-based polymer is polymerized in the presence of the first ethylene-based polymer.

In one embodiment, the polymerization pressure in Step (A) is at least 18,000 psi.

In one embodiment, the polymerization pressure in Step (A) is at least 22,000 psi.

In one embodiment, the polymerization pressure in Step (A) is at least 26,000 psi.

In one embodiment, the polymerization pressure in Step (A) is from 20,000 psi to 45,000 psi.

In one embodiment, the polymerization pressure in Step (A) is from 25,000 psi to 35,000 psi.

In one embodiment, the polymerization pressure in Step (A) and Step (B) is from 15,000 to 60,000 psi, preferably from 20,000 to 40,000 psi.

In one embodiment, the first polymerization conditions include a pressure of at least 14,000 psi and a temperature of at least 195° C.

In one embodiment, the second polymerization conditions include a pressure of at least 20,000 psi and a temperature of at least 180° C.

In one embodiment, hydrogen gas is not introduced into the Step (A) polymerization.

In one embodiment, hydrogen gas is not introduced into the Step (B) polymerization.

In one embodiment, hydrogen gas is not introduced into either the Step (A) or Step (B) polymerization.

In one embodiment, the molecular catalyst is selected from the group consisting of constrained geometry catalysts and post-metallocene catalysts.

In one embodiment, the molecular catalyst is a zirconium complex of a polyvalent aryloxyether corresponding to the Structure A:

(Structure A)

where $R^{20}$ independently in each occurrence is a divalent aromatic or inertly substituted aromatic group, each having from 5 to 20 atoms not counting hydrogen;

$T^3$ is a divalent hydrocarbon or a silane group, each having from 1 to 20 atoms not counting hydrogen, or an inertly substituted derivative thereof; and $R^D$ independently in each occurrence is a monovalent ligand group having from 1 to 20 atoms, not counting hydrogen, or two $R^D$ groups together are a divalent ligand group having from 1 to 40 atoms, not counting hydrogen.

In one embodiment, the molecular catalyst is a zirconium complex of a polyvalent aryloxyether corresponding to the Structure B:

(Structure B)

where $M^3$ is Hf or Zr, preferably Zr;

$Ar^4$ independently at each occurrence is a substituted $C_{9-20}$ aryl group, wherein the substituents, independently at each occurrence, are selected from the group consisting of alkyl; cycloalkyl; and aryl groups; and halo-, trihydrocarbylsilyl- and halohydrocarbyl-substituted derivatives thereof, with the proviso that at least one substituent lacks co-planarity with the aryl group to which it is attached;

$T^4$ is a $C_{2-20}$ alkylene, cycloalkylene or cycloalkenylene group, or an inertly substituted derivative thereof;

$R^{21}$ independently at each occurrence is hydrogen, halo, hydrocarbyl, trihydrocarbylsilyl, trihydrocarbylsilylhydrocarbyl, alkoxy or di(hydrocarbyl)amino group of up to 50 atoms not counting hydrogen;

$R^3$ independently at each occurrence is hydrogen, halo, hydrocarbyl, trihydrocarbylsilyl, trihydrocarbylsilylhydrocarbyl, alkoxy or amino of up to 50 atoms not counting hydrogen, or two $R^3$ groups on the same arylene ring together or an $R^3$ and an $R^{21}$ group on the same or different arylene ring together form a divalent ligand group attached to the arylene group in two positions or join two different arylene rings together; and $R^D$, independently at each occurrence is a halo or a hydrocarbyl or trihydrocarbylsilyl group of up to 20 atoms not counting hydrogen, or 2 $R^D$ groups together are a hydrocarbylene, hydrocarbadiyl, diene, or poly(hydrocarbyl)silylene group, especially where the reaction of step (B) occurs by polymerization.

In one embodiment, the molecular catalyst further comprises at least one cocatalyst.

In one embodiment, the molecular catalyst further comprises a cocatalyst that is at least one of (i) polymeric or oligomeric aluminoxane, and (ii) an inert, noncoordinating, boron compound.

In one embodiment, the molecular catalyst is soluble in supercritical ethylene.

In one embodiment, the molecular catalyst is active at polymerization temperature greater than, or equal to, 200° C.

In one embodiment, the molecular catalyst is active at polymerization temperature greater than, or equal to, 210° C.

In one embodiment, the molecular catalyst is active at polymerization temperature greater than, or equal to, 220° C.

In one embodiment, the molecular catalyst is selected from the group consisting of constrained geometry catalysts and post metallocene catalysts (e.g., polyvalent aryloxyether compounds).

In one embodiment, the molecular catalyst is selected from the group consisting of polyvalent aryloxyether catalysts (e.g., polyvalent aryloxyether compounds). Some examples of polyvalent aryloxyether catalysts are described in U.S. Publication No. 2005/0164872 and International Publication No. WO 2007/136494; each incorporated herein by reference.

In one embodiment, the molecular catalyst is selected from the group consisting of constrained geometry catalysts. Some examples of constrained geometry catalysts are described in U.S. Pat. Nos. 5,272,236 and 5,278,272; each incorporated herein by reference.

In one embodiment, the catalyst has a chain transfer rate to ethylene of over 50% based on the total amount of chain transfer.

In one embodiment, catalyst concentration in Step 1 is from 0.001 to 2 moles per parts per million (mol ppm), preferably from 0.001 to 0.1 mol ppm, based on the total amount of ethylene added to the polymerization process.

The molecular catalyst may comprise a combination of two or more embodiments as described herein.

In one embodiment, the first ethylene-based polymer is polymerized in the presence of an alumoxane cocatalyst. In a further embodiment, the alumoxane cocatalyst is present in an amount less than 50 mol ppm, preferably less than 40 mol ppm, and more preferably less than 30 mol ppm, based on the total amount of ethylene added to the polymerization process.

In one embodiment, step B further comprises a chain transfer agent. In a further embodiment, the hydrocarbon chain transfer agent of Step B comprises from three to five carbon atoms.

In one embodiment, the hydrocarbon chain transfer agent of Step B is a non-aromatic compound.

In one embodiment, the hydrocarbon chain transfer agent of Step B is selected from the groups consisting of C3-C5 aliphatic alkanes, C3-C5 aliphatic alkenes, and C3-C5 aliphatic alkynes.

In one embodiment, the hydrocarbon chain transfer agent of Step B is added to the reactor in an amount from greater than, or equal to, 0.2 mole percent (mol %), based on the amount of ethylene added to this reactor.

In one embodiment, the hydrocarbon chain transfer agent of Step B is added to the reactor in an amount from greater than, or equal to, 0.5 mol %, based on the amount of ethylene added to this reactor.

In one embodiment, the hydrocarbon chain transfer agent of Step B is added to the reactor in an amount from greater than, or equal to, 1 mol %, based on the amount of ethylene added to this reactor.

In one embodiment, the hydrocarbon chain transfer agent of Step B is added to the reactor in an amount from less than, or equal to, 4 mol %, based on the amount of ethylene added to this reactor.

In one embodiment, the hydrocarbon chain transfer agent of Step B is added to the reactor in an amount from less than, or equal to, 3.5 mol %, based on the amount of ethylene added to this reactor.

In one embodiment, the hydrocarbon chain transfer agent of Step B is added to the reactor in an amount from less than, or equal to, 3 mol %, based on the amount of ethylene added to this reactor.

In one embodiment, the hydrocarbon chain transfer agent of Step B is added to the reactor in an amount from 1 to 3.5 mol %, based on the amount of ethylene added to this reactor.

In one embodiment, the hydrocarbon chain transfer agent of Step B is added to the reactor in an amount from 2 to 3 mol %, based on the amount of ethylene added to this reactor.

In one embodiment, the hydrocarbon chain transfer agent is present in Step B from 0.5 to 10 mol %, preferably from 0.5 to 3 mol %, based on the amount of ethylene added to this reactor.

The hydrocarbon chain transfer agent may comprise a combination of two or more embodiments as described herein.

In one embodiment, for Structure I, $R_1$ and $R_4$ are phenyl.

In one embodiment, for Structure I, the at least one carbon-carbon (C—C) initiator is selected from the group consisting of 3,4-diethyl-3,4-diphenyl hexane and 3,4-dipropyl-3,4-diphenyl hexane.

In one embodiment, the second polymerization conditions are free of peroxides. In one embodiment, the polymerization temperature in Step (A) is greater than, or equal to, 195° C., or greater than, or equal to, 200° C., or greater than, or equal to, 210° C., or greater than, or equal to, 220° C.

In one embodiment, the polymerization temperature in Step (A) is from 195° C. to 260° C. In one embodiment, the polymerization temperature in Step (A) is from 200° C. to 240° C. In one embodiment, the polymerization temperature in Step (A) is from 210° C. to 230° C.

In one embodiment, the polymerization temperature in Step (B) is from 180° C. to 350° C., or from 190° C. to 300° C., or from 200° C. to 280° C.

In one embodiment, no hydrogen is added to Step (A). In one embodiment, no hydrogen is added to Step (B). In one embodiment, no hydrogen is added to Step (A) or Step (B).

In one embodiment, the process does not comprise a boron-containing compound.

In one embodiment, the process further comprises polymerizing a third ethylene-based polymer.

In one embodiment, at least one alkyl aluminum is added to the process after Step (B).

An alkyl aluminum is a compound with at least one aluminum attached to one or more alkyl groups, such as triethylaluminum or triisobutylaluminum. These also include aluminoxane type species such as MAO or MMAO-3A (CAS #-146905-79-5).

In one embodiment, at least one polyalkylene glycol is added to the process after Step (B). In a further embodiment, the polyalkylene glycol has a number average molecular weight of at least 200 grams per mole (g/mol), or at least 250 g/mol, or at least 300 g/mol.

In one embodiment, the polyalkylene glycol is a compound of formula $HO(CH2CHRO)_nH$, where R is an alkyl group or hydrogen. Preferably R=H (polyethylene glycol). Preferably n is from 3 to 10 repeat units.

In one embodiment, a non-volatile catalyst kill is used to deactivate the catalyst before it exits the final reactor in the polymerization process.

In one embodiment, the polymerization process is a continuous process.

In one embodiment, the first ethylene-based polymer is a polyethylene homopolymer. In one embodiment, the second ethylene-based polymer is a polyethylene homopolymer. In one embodiment, the first ethylene-based polymer is a polyethylene homopolymer, and the second ethylene-based polymer is a polyethylene homopolymer.

In one embodiment, the inventive process takes place in at least one autoclave reactor.

In one embodiment, the inventive process takes place in at least one tubular reactor.

In one embodiment, the inventive process takes place in at least one autoclave reactor and in at least one tubular reactor. In a further embodiment, the at least one autoclave reactor and the at least one tubular reactor are connected in series.

The invention also provides a polymer composition formed by an inventive process.

In one embodiment, the polymer composition formed by the inventive process has a density of greater than, or equal to, 0.90 grams per cubic centimeter (g/cc).

In one embodiment, the polymer composition formed by the inventive process has a melt index (I2) from 0.1 to 100 decagrams per minute (dg/min).

In one embodiment, the polymer composition has a percent crystallinity of at least 45 percent, as determined by differential scanning calorimetry (DSC).

In one embodiment, the polymer composition has a percent crystallinity of at least 50 percent, as determined by DSC.

In one embodiment, the polymer composition has at least one melting point greater than 115° C., or greater than 120° C., or greater than 125° C., as determined by DSC.

In one embodiment, the polymer composition has a melting point greater than 115° C., or greater than 120° C., or greater than 125° C., as determined by DSC.

In one embodiment, the polymer composition has a heat of fusion greater than 165 J/g, or greater than 170 J/g, as determined by DSC.

In one embodiment, the polymer composition has a carbonyl ratio <0.040, or <0.035, or <0.030, or <0.025, or <0.020, or <0.015.

In one embodiment, the polymer composition has an aluminum content ≤60 mass ppm, or ≤55 mass ppm, or ≤50 mass ppm, or ≤45 mass ppm, or ≤40 mass ppm, or ≤35 mass ppm, based on the weight of the polymer composition, as determined by the neutron activation method.

In one embodiment, the polymer composition has a fraction as determined by Crystallization Elution Fractionation (CEF), at a temperature of at least 85° C., of at least 5 weight percent (wt %, based on weight of polymer composition), and which has a trefBR value (a long chain branching parameter determined from CEF data as described in Yau, Wallace W., "Examples of Using 3D-GPC-TREF for Polyolefin Characterization", Macromol. Symp. 2007, 257, 29-45), of greater than 0.5.

In one embodiment, the first ethylene-based polymer has a density from 0.920 to 0.95 g/cc.

In one embodiment, the first ethylene-based polymer has a density from 0.930 to 0.970 g/cc, or 0.930 to 0.960 g/cc, or 0.930 to 0.950 g/cc, or 0.935 to 0.945 g/cc.

In one embodiment, the first ethylene-based polymer has a melt index (I2) from 0.1 to 100 dg/min.

In one embodiment, the first ethylene-based polymer has a melt index (I2) from 0.5 to 30 dg/min.

In one embodiment, the first ethylene-based polymer has a melt index (I2) from 0.1 to 20 dg/min, or 0.3 to 15 dg/min, or 0.5 to 10 dg/min, or 0.8 to 5 dg/min.

In one embodiment, the second ethylene-based polymer has a density from 0.920 to 0.95 g/cc.

In one embodiment, the second ethylene-based polymer has a density from 0.930 to 0.970 glee, or 0.930 to 0.960 g/cc, or 0.930 to 0.950 g/cc, or 0.935 to 0.945 g/cc.

In one embodiment, the second ethylene-based polymer has a melt index (I2) from 0.1 to 100 dg/min.

In one embodiment, the second ethylene-based polymer has a melt index (I2) from 0.5 to 30 dg/min.

In one embodiment, the second ethylene-based polymer has a melt index (I2) from 0.1 to 20 dg/min, or 0.3 to 15 dg/min, or 0.5 to 10 dg/min, or 0.8 to 5 dg/min.

In one embodiment, the invention is a composition comprising an ethylene-based polymer formed by the process of any one of the preceding embodiments.

In one embodiment, the polymer composition has a density from 0.920 to 0.95 g/cc.

In one embodiment, the polymer composition has a density from 0.930 to 0.970 g/cc, or 0.930 to 0.960 glee, or 0.930 to 0.950 glee, or 0.935 to 0.945 g/cc.

In one embodiment, the polymer composition has a melt index (I2) from 0.1 to 100 dg/min.

In one embodiment, the polymer composition has a melt index (I2) from 0.5 to 30 dg/min.

In one embodiment, the polymer composition has a melt index (I2) from 0.1 to 20 dg/min, or 0.3 to 15 dg/min, or 0.5 to 10 dg/min, or 0.8 to 5 dg/min.

In one embodiment, the polymer composition comprises ≥50 wt %, or ≥60 wt %, or ≥70 wt %, or ≥80 wt % of the second ethylene-based polymer, based on the weight of the polymer composition.

In one embodiment, the polymer composition comprises ≥85 wt %, or ≥90 wt %, or ≥95 wt %, or ≥98 wt % of the second ethylene-based polymer, based on the weight of the polymer composition.

In one embodiment, an inventive polymer composition may comprise a combination of two or more embodiments as described herein.

The invention also provides a composition comprising an inventive polymer composition and at least one additive.

An inventive composition may comprise a combination of two or more embodiments as described herein.

The invention also provides an article comprising at least one component formed from an inventive polymer composition or an inventive composition.

In one embodiment, the C—C free-radical initiator is present in an amount greater than, or equal to, 0.001 grams per kilogram (g/kg), further greater than 0.005 g/kg, further greater than 0.008 g/kg, further greater than 0.01 g/kg, of the ethylene fed to the polymerization reaction.

In one embodiment, the C—C free-radical initiator has a decomposition temperature of greater than or equal to (≥)125° C., or ≥130° C., or ≥150° C., or ≥180° C., or ≥200° C., or ≥250° C., based on differential scanning calorimetry (DSC) measurements.

In one embodiment, the process comprises contacting ethylene and, optionally, one or more alpha-olefin comonomers, with at least two C—C free-radical initiators.

In one embodiment the invention is a composition comprising an ethylene-based polymer formed by the process of any one of the previous embodiments.

In one embodiment the polymer composition comprises ≤50 wt %, further ≤20 wt %, further ≤10 wt % of a low density polyethylene, e.g., LDPE, and wherein the low density polyethylene is formed in Step B.

In one embodiment the polymer composition comprises ≥1 wt %, further ≥2 wt %, further ≥5 wt % of a low density polyethylene, e.g., LDPE, and wherein the low density polyethylene is formed in Step B.

In one embodiment the polymer composition of this invention has a dissipation factor of no greater than $1.49 \times 10^{-4}$ radian at 2.47 GHz, preferably no greater than $1.45 \times 10^{-4}$ radian at 2.47 GHz and more preferably no greater than $1.43 \times 10^{-4}$ radian at 2.47 GHz.

In one embodiment, the melt index ($I_2$, 190° C./2.16 kg) of the polymer composition is from 0.1-100 g/10 min, or from 0.25-50 g/10 min, or from 0.5-20 g/10 min.

In one embodiment, the polymer composition has a density from 0.90 to 0.97 g/cc, preferably from 0.91 to 0.96 g/cc, more preferably from 0.920 to 0.950 g/cc.

In one embodiment, the polymer composition has a molecular weight distribution from the conventional calibration of triple detector gel permeation chromatography (GPC) from 3 to 20, or from 3.5 to 15, or from 5 to 10.

In one embodiment the polymer composition comprises ≥0.1 amyl (C5) branches per 1000 carbon atoms, or ≥0.5 amyl branches per 1000 carbon atoms, or >1 amyl branches per 1000 carbon atoms as determined by 13C NMR.

In one embodiment the polymer composition comprises less than (<) 100 weight ppm oxygen, preferably <50 weight ppm oxygen and more preferably <1 weight ppm oxygen as determined by mass balance of oxygenated components added to the polymerization process.

In one embodiment, the invention is a composition comprising (i) a polymer composition made by the process of this invention, and (ii) one or more additives.

An inventive composition may comprise a combination of two or more embodiments as described herein.

In one embodiment the invention is a composition comprising the second ethylene-based polymer of this invention.

In one embodiment, the second ethylene-based polymer is formed from a reaction mixture comprising the first ethylene-based polymer, ethylene and the C—C free radical initiator.

In one embodiment the composition comprising the second ethylene-based polymer of this invention also comprises one or more olefin-based polymers.

The invention also provides an article comprising at least one component formed from an inventive composition as described herein. In a further embodiment, the article is a film or a coating.

An inventive article may comprise a combination of two or more embodiments as described herein.

C—C Free Radical Initiators

The carbon-carbon ("C—C") free radical initiators used in the practice of this invention comprise only carbon and hydrogen, and have Structure I:

(Structure I)

wherein $R_1$, $R_2$, $R_3$, $R_4$, $R_5$ and $R_6$ are each, independently, hydrogen or a hydrocarbyl group and wherein, optionally, two or more R groups ($R_1$, $R_2$, $R_3$, $R_4$, $R_5$ and $R_6$) form a ring structure, with the provisos that at least one of $R_2$ and $R_5$, and at least one of $R_3$ and $R_6$ is a hydrocarbyl group of at least two carbon atoms.

In one embodiment, one or more of the $R_1$-$R_6$ groups are aliphatic.

In one embodiment, one or more of the $R_1$-$R_6$ groups are alkyl.

In one embodiment, one or more of the $R_1$-$R_6$ groups are aryl.

In one embodiment, two or more of the $R_1$-$R_6$ groups are aryl.

In one embodiment, $R_1$ and $R_4$ are aryl, preferably phenyl.

In one embodiment, $R_1$ and $R_4$ are aryl, and one of $R_2$ and $R_5$, and one of $R_3$ and $R_6$ is hydrogen.

In one embodiment, $R_1$ and $R_4$ are aryl, and one of $R_2$ and $R_5$ and one of $R_3$ and $R_6$ is a $C_2$-$C_{10}$ alkyl and the other of $R_2$ and $R_5$ and the other of $R_3$ and $R_6$ is hydrogen.

In one embodiment $R_1$ and $R_4$ are the same or different aryl radicals. In a further embodiment, $R_1$ and $R_4$ are each phenyl, e.g., Structure II; and wherein $R_2$, $R_3$, $R_5$ and $R_6$ are each as described above:

(Structure II)

In one embodiment, $R_2$-$R_3$ and $R_5$-$R_6$ are the same or different alkyl radicals, more preferably the same or different $C_{1-6}$ alkyl radicals, and even more preferably the same $C_{1-4}$ straight chain alkyl radical.

Representative C—C initiators include, but are not limited to, the following Structures III-VIII, as follows: 3,4-dimethyl-3,4-diphenyl hexane (Structure III), (Structure III)

and, 3,4-diethyl-3,4-diphenyl hexane (Structure IV), (Structure IV)

2,7-dimethyl-4,5diethyl-4,5-diphenyl octane (DBuDPH) (Structure V), (Structure V)

3,4-dibenzyl-3,4-ditolyl hexane (DBnDTH) (Structure VI),

Structure VI 3,4-diethyl-3,4-di(dimethylphenyl) hexane (Structure VII),

Structure VII and, 3,4-dibenzyl-3,4-diphenyl hexane (Structure VIII),

Structure VIII

Other C—C initiators include those of Structure I and described in such publications as WO 2012/096962, WO 2012/074812, US 2010/0108357, EP 1 944 327, U.S. Pat.

Nos. 5,268,440, 6,967,229 and US 2006/0047049. The C—C initiators can be used alone or in combination with one another.

In one embodiment, the C—C free-radical initiator is present in an amount greater than, or equal to, 0.001 grams per kilogram (g/kg), further greater than 0.005 g/kg, further greater than 0.008 g/kg, further greater than 0.01 g/kg, of the ethylene fed to the polymerization reaction. While the only limitation on the maximum amount of C—C initiator used in the practice of this invention is a function of process economics and efficiency, typically the maximum amount of C—C initiator used in the practice of this invention does not exceed 1 g/kg, more typically does not exceed 0.1 g/kg and even more typically does not exceed 0.05 g/kg, of the ethylene fed to the polymerization reaction.

A C—C initiator may comprise a combination of two or more embodiments as described herein. In those embodiments in which the C—C initiator is used in combination with one or more other C—C initiators, only one of the C—C initiators must have at least one of $R_2$ and $R_5$, and at least one of $R_3$ and $R_6$ as a hydrocarbyl group of at least two carbon atoms. In such embodiments, a C—C initiator of Structure I comprises at least 25 wt %, preferably at least 50 wt %, more preferably more than 50 wt % and even more preferably at least 75 wt %, of the total amount of C—C initiator used in the process.

Polymerization

Fouling in high pressure reactors can occur due to high molecular weight background LDPE, initiated either thermally or by adventitious oxygen in the system. A hydrocarbon chain transfer agent can be used to reduce the molecular weight and decrease the fouling tendencies of this background LDPE.

In a commercial process, typically all polar compounds produced in the reactor will recycle to the front of the reactor and deactivate a molecular catalyst. These polar compounds can include decomposition products of the peroxides typically used to make the LDPE portion of the polymer composition or polar catalyst kill added after the first reactor to prevent further polymerization. For the inventive processes described herein, these impurities can be avoided by using a carbon-carbon free radical initiator as described above.

The inventive process can be operated in either one or more tube reactors, autoclave reactors, or autoclave/tube configurations. In one embodiment, the split between the first ethylene-based polymer and the second ethylene-based polymer is controlled in the tube process by using different lengths of the tube for each reaction zone. In another embodiment, in an autoclave/tube or autoclave process, the split between different zones is controlled by dividing the autoclave into separate zones with baffles. Each zone can be used to produce either the first ethylene-based polymer or the second ethylene-based polymer.

Ethylene used for the production of the ethylene-based polymers may be purified ethylene, which is obtained by removing polar components from a loop recycle stream and from fresh ethylene.

In one embodiment, the first ethylene-based polymer is a polyethylene homopolymer.

In one embodiment, the first ethylene-based polymer is an ethylene/alpha-olefin copolymer.

In another embodiment, the first ethylene-based polymer is a linear low density polyethylene.

In another embodiment, the first ethylene-based polymer comprises ethylene and one or more comonomers, and preferably one comonomer. Comonomers include, but are not limited to, α-olefin comonomers, typically having no more than 20 carbon atoms. For example, the α-olefin comonomers may have 3 to 10 carbon atoms; or in the alternative, the α-olefin comonomers may have 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene.

In one embodiment, the second ethylene-based polymer is a polyethylene homopolymer.

In another embodiment, the polymer composition comprises a free, e.g., unreacted with a branching agent or CTA, low density polyethylene.

In another embodiment, the second ethylene-based polymer comprises, in polymerized form, ethylene and one or more comonomers, and preferably one comonomer. Comonomers include, but are not limited to, α-olefin comonomers, typically having no more than 20 carbon atoms. For example, the α-olefin comonomers, for example, may have 3 to 10 carbon atoms; or in the alternative, the α-olefin comonomers, for example, may have 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene.

Additives

A polymer composition may comprise at least one additive. Additives include, but are not limited to, stabilizers, plasticizers and fillers. Stabilizers include, for example, antioxidants, such as IRGANOX™ 1010 and IRGAFOS™ 168 (Ciba Specialty Chemicals; Glattbrugg, Switzerland). In general, polymers are treated with one or more stabilizers before an extrusion or other melt processes. In other embodiment processes, other polymeric additives include, but are not limited to, ultraviolet light absorbers, antistatic agents, pigments, dyes, nucleating agents, fillers, slip agents, fire retardants, plasticizers, processing aids, lubricants, stabilizers, smoke inhibitors, viscosity control agents and anti-blocking agents. The ethylene-based polymer composition may, for example, comprise less than 10 percent by the combined weight of one or more additives, based on the weight of the final composition.

Fillers include, but are not limited to, organic or inorganic particles, including clays, talc, titanium dioxide, zeolites, powdered metals, organic or inorganic fibers, including carbon fibers, silicon nitride fibers, steel wire or mesh, and nylon or polyester cording, nano-sized particles, clays.

The polymer compositions may be blended or mixed with other polymers, such as other olefin-based polymers. Polymers include, for example, thermoplastic and non-thermoplastic polymers including natural and synthetic polymers. Exemplary polymers for blending include polypropylene, (both impact modifying polypropylene, isotactic polypropylene, atactic polypropylene, and random ethylene/propylene copolymers), various types of polyethylene, including high pressure, free-radical LDPE, Ziegler-Natta LLDPE, metallocene PE, including multiple reactor PE ("in reactor" blends of Ziegler-Natta PE and metallocene PE, such as products disclosed in U.S. Pat. No. 6,545,088 (Kolthammer, et al.); U.S. Pat. No. 6,538,070 (Cardwell, et al.); U.S. Pat. No. 6,566,446 (Parikh, et al.); U.S. Pat. No. 5,844,045 (Kolthammer, et al.); U.S. Pat. No. 5,869,575 (Kolthammer, et al.); and U.S. Pat. No. 6,448,341 (Kolthammer, et al.)), ethylene-vinyl acetate (EVA), ethylene/vinyl alcohol copolymers, polystyrene, impact modified polystyrene, ABS, styrene/butadiene block copolymers and hydrogenated derivatives thereof (SBS and SEBS), and thermoplastic polyurethanes. Homogeneous polymers such as olefin plastomers and elastomers, ethylene and propylene-based copolymers (for example, polymers available under the trade designation VERSIFY™ Plastomers & Elastomers (The Dow Chemical Company), SURPASS™ (Nova Chemicals), and VISTAMAXX™ (ExxonMobil Chemical Co.)) can also be used.

Applications

The polymer compositions may be employed in a variety of conventional thermoplastic fabrication processes to produce useful articles, including objects comprising at least one film layer, such as a monolayer film, or at least one layer in a multilayer film prepared by cast, blown, calendered, or extrusion coating processes; molded articles, such as blow molded, injection molded, or roto-molded articles; extrusions; fibers; and woven or non-woven fabrics.

Definitions

The term "composition," as used herein, includes a mixture of materials which comprise the composition, as well as reaction products and decomposition products formed from the materials of the composition.

The term "polymer composition," as used herein, refers to a composition that comprises at least one ethylene-based polymer, and typically comprises at least two ethylene-based polymers. These compositions may also include unreacted first ethylene-based polymer, as described herein, and/or a free radically polymerized ethylene-based polymer (for example, LDPE).

The second ethylene-based polymer, as described herein, is formed from at least the following: a) the first ethylene-based polymer, as described herein, and b) ethylene. In a preferred embodiment, the amount of polymerized ethylene in the second ethylene-based polymer is greater than 60 weight percent, preferably greater than 80 weight percent, preferably greater than 90 weight percent, based on the weight of the second ethylene-based polymer.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. Trace amounts of impurities may be incorporated into and/or within a polymer.

The term "interpolymer," as used herein, refers to polymers prepared by the polymerization of at least two different types of monomers. The generic term interpolymer thus includes copolymers (employed to refer to polymers prepared from two different types of monomers), and polymers prepared from more than two different types of monomers.

The term, "olefin-based polymer," as used herein, refers to a polymer that comprises, in polymerized form, a majority amount of olefin monomer, for example ethylene or propylene (based on the weight of the polymer), and optionally may comprise one or more comonomers.

The term, "ethylene-based polymer," as used herein, refers to a polymer that comprises, in polymerized form, a majority amount of ethylene monomer (based on the weight of the polymer), and optionally may comprise one or more comonomers.

The term, "ethylene/α-olefin interpolymer," as used herein, refers to an interpolymer that comprises, in polymerized form, a majority amount of ethylene monomer (based on the weight of the interpolymer), and at least one α-olefin.

The term, "ethylene/α-olefin copolymer," as used herein, refers to a copolymer that comprises, in polymerized form, a majority amount of ethylene monomer (based on the weight of the copolymer), and an α-olefin, as the only two monomer types.

The term "hydrocarbon," as used herein, refers to a chemical compound that comprises only hydrogen and carbon atoms.

The term "molecular catalyst," as used herein, refers to a catalyst that can be defined by one molecular structure. This term does not include Ziegler-Natta catalysts, which can be defined by more than one molecular structure.

The term "boron-containing compound," as used herein, refers to a chemical compound that contains at least one boron atom.

The term "reaction zone," as used herein, refers to a zone in a reactor where the polymerization reaction is initiated by the addition of a catalyst and/or cocatalyst and/or free radicals and/or components which dissociate into and/or generate free radicals.

The term "first polymerization conditions" as used herein, refers to the conditions of a reaction zone, for example, a first reaction zone, in which ethylene is contacted with the molecular catalyst to produce the first ethylene-based polymer. The conditions include the temperature and pressure of the first reaction zone as described herein.

The term "second polymerization conditions" as used herein, refers to the conditions of a reaction zone, for example, a second reaction zone, in which the first ethylene-based polymer is contacted with additional ethylene and the carbon-carbon free radical initiator to produce the second ethylene-based polymer. The conditions include the temperature and pressure of the second reaction zone as described herein.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

Unless stated to the contrary, all test methods are current as of the filing date of this application.

Density

Samples for density measurements were prepared according to ASTM D 4703-10. Samples were pressed at 374° F. (190° C.), for five minutes, at 10,000 psi (68 MPa). The temperature was maintained at 374° F. (190° C.) for the above five minutes, and then the pressure was increased to 30,000 psi (207 MPa) for three minutes. This was followed by a one minute hold at 70° F. (21° C.) and 30,000 psi (207 MPa). Measurements were made within one hour of sample pressing using ASTM D792-08, Method B.

Melt Index

Melt index (MI 12 or $I_2$) was measured in accordance with ASTM D 1238-10, Condition 190° C./2.16 kg, Method B, and was reported in grams eluted per 10 minutes.

Differential Scanning Calorimetry

Differential Scanning calorimetry (DSC) can be used to measure the melting and crystallization behavior of a polymer over a wide range of temperature. For example, the TA Instruments Q1000 DSC, equipped with an RCS (refrigerated cooling system) and an autosampler is used to perform this analysis. During testing, a nitrogen purge gas flow of 50 ml/min is used. Each sample is melt pressed into a thin film at about 175° C.; the melted sample is then air-cooled to room temperature (~25° C.). A 3-10 mg, "6 mm diameter" specimen is extracted from the cooled polymer, weighed, placed in a light aluminum pan (~50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C., and held isothermal for 3 minutes, in order to remove its thermal history. Next, the sample is cooled to ~40° C., at a 10° C./minute cooling rate, and held isothermal at ~40° C. for 3 minutes. The sample is then heated to 150° C. (this is the "second heat" ramp) at a 10° C./minute heating rate. The cooling and second heating curves are recorded. The cool curve is analyzed by setting baseline endpoints from the beginning of crystallization to ~20° C. The heat curve is analyzed by setting baseline endpoints from ~20° C. to the end of melt. The values determined are peak melting temperature ($T_m$), peak crystallization temperature ($T_c$), heat of fusion ($H_f$) (in Joules per gram), and the calculated percent (%) crystallinity for polyethylene samples using the equation below:

% Crystallinity=(($H_f$)/(292 J/g))×100.

The heat of fusion ($H_f$) and the peak melting temperature are reported from the second heat curve. Peak crystallization temperature is determined from the cooling curve.

Triple Detector Gel Permeation Chromatography
(TDGPC)–Conventional GPC Data

A Triple Detector Gel Permeation Chromatography (3D-GPC or TDGPC) system consisting of a Polymer Laboratories (now Agilent) high temperature chromatograph Model 220, equipped with a 2-angle laser light scattering (LS) detector Model 2040 (Precision Detectors, now Agilent), an IR-4 infra-red detector from Polymer Char (Valencia, Spain), and a 4-capillary solution viscometer (DP) (Viscotek, now Malvern) was used. Data collection was performed using Polymer Char DM 100 data acquisition box and related software (Valencia, Spain). The system was also equipped with an on-line solvent degassing device from Polymer Laboratories (now Agilent).

High temperature GPC columns consisting of four 30 cm, 20 um mixed A LS columns from Polymer Laboratories (now Agilent) were used. The sample carousel compartment was operated at 140° C., and the column compartment was operated at 150° C. The samples were prepared at a concentration of 0.1 grams of polymer in 50 milliliters of solvent. The chromatographic solvent and the sample preparation solvent was 1,2,4-trichlorobenzene (TCB) containing 200 ppm of 2,6-di-tert-butyl-4methylphenol (BHT). The solvent was sparged with nitrogen. The polymer samples were gently stirred at 160° C. for four hours. The injection volume was 200 microliters. The flow rate through the GPC was set at 1.0 ml/minute.

Column calibration and sample molecular weight calculations were performed using Polymer Char "GPC One" software. Calibration of the GPC columns was performed with 21 narrow molecular weight distribution polystyrene standards. The molecular weights of the polystyrene standards ranged from 580 to 8,400,000 g/mol, and were arranged in 6 "cocktail" mixtures, with at least a decade of separation between the individual molecular weights.

The peak molecular weights of polystyrene standards were converted to polyethylene molecular weights using the following equation (as described in Williams and Ward, J. Polym. Sci., Polym. Let., 6, 621 (1968)): $M_{polyethylene}=A \cdot (M_{polystyrene})^B$, here B has a value of 1.0, and the experimentally determined value of A is around 0.38 to 0.44.

The column calibration curve was obtained by fitting a first order polynomial to the respective polyethylene-equivalent calibration points obtained from the above Equation to the observed elution volumes.

Number, weight, and z-average molecular weights were calculated according to the following equations:

$$\overline{Mn} = \frac{\sum_i Wf_i}{\sum_i (Wf_i/M_i)} \quad \overline{Mw} = \frac{\sum_i (Wf_i * M_i)}{\sum_i Wf_i} \quad \overline{Mz} = \frac{\sum_i (Wf_i * M_i^2)}{\sum_i (Wf_i * M_i)},$$

where, $Wf_i$ is the weight fraction of the i-th component and $M_i$ is the molecular weight of the i-th component. The molecular weight distribution (MWD) was expressed as the ratio of the weight average molecular weight (Mw) to the number average molecular weight (Mn).

The A value was determined by adjusting the A value in the Williams and Ward Equation until Mw, the weight average molecular weight calculated using the above Equation, and the corresponding retention volume polynomial agreed with the independently determined value of Mw obtained in accordance with the linear homopolymer reference with known weight average molecular weight of 115,000 g/mole.

gpcBR Branching Index by Triple Detector GPC (TDGPC)

The gpcBR branching index was determined by first calibrating the light scattering, viscosity, and concentration detectors as described previously. Baselines were then subtracted from the light scattering, viscometer, and concentration chromatograms. Integration windows were then set, to ensure integration of all of the low molecular weight retention volume range in the light scattering and viscometer chromatograms that indicate the presence of detectable polymer from the refractive index chromatogram. Linear polyethylene standards were then used to establish polyethylene and polystyrene Mark-Houwink constants. Upon obtaining the constants, the two values were used to construct two linear reference conventional calibrations for polyethylene molecular weight and polyethylene intrinsic viscosity as a function of elution volume, as shown in Equations (9) and (10):

$$M_{PE} = \left(\frac{K_{PS}}{K_{PE}}\right)^{1/\alpha_{PE}+1} \cdot M_{PS}^{\alpha_{PS}+1/\alpha_{PE}+1}, \quad \text{(EQN 9)}$$

$$[\eta]_{PE} = K_{PS} \cdot M_{PS}^{\alpha+1}/M_{PE}. \quad \text{(EQN 10)}$$

The gpcBR branching index is a robust method for the characterization of long chain branching as described in Yau, Wallace W., "Examples of Using 3D-GPC-TREF for Polyolefin Characterization," Macromol. Symp., 2007, 257, 29-45. The index avoids the "slice-by-slice" 3D-GPC calculations traditionally used in the determination of g' values and branching frequency calculations, in favor of whole polymer detector areas. From TDGPC data, one can obtain the sample bulk absolute weight average molecular weight (Mw, Abs) by the light scattering (LS) detector, using the peak area method. The method avoids the "slice-by-slice" ratio of light scattering detector signal over the concentration detector signal, as required in a traditional g' determination.

With TDGPC, sample intrinsic viscosities were also obtained independently using Equations (11). The area calculation in this case offers more precision, because, as an overall sample area, it is much less sensitive to variation caused by detector noise and 3D-GPC settings on baseline and integration limits. More importantly, the peak area calculation was not affected by the detector volume offsets. Similarly, the high-precision, sample intrinsic viscosity (IV) was obtained by the area method shown in Equation (11):

$$IV = [\eta] = \sum_i w_i IV_i = \qquad \text{(EQN 11)}$$

$$\sum_i \left(\frac{C_i}{\sum_i C_i}\right) IV_i = \frac{\sum_i C_i IV_i}{\sum_i C_i} = \frac{\sum_i DP_i}{\sum_i C_i} = \frac{DP \text{ Area}}{\text{Conc. Area}},$$

where DPi stands for the differential pressure signal monitored directly from the online viscometer.

To determine the gpcBR branching index, the light scattering elution area for the sample polymer was used to determine the molecular weight of the sample. The viscosity detector elution area for the sample polymer was used to determine the intrinsic viscosity (IV or [η]) of the sample.

Initially, the molecular weight and intrinsic viscosity for a linear polyethylene standard sample, such as SRM1475a or an equivalent, were determined using the conventional calibrations ("cc") for both molecular weight and intrinsic viscosity as a function of elution volume:

$$[\eta]_{CC} = \sum_i \left(\frac{C_i}{\sum_i C_i}\right) IV_i = \sum_i w_i IV_{cc,i}. \qquad \text{(EQN 12)}$$

Equation (13) was used to determine the gpcBR branching index:

$$gpcBR = \left[\left(\frac{[\eta]_{CC}}{[\eta]}\right) \cdot \left(\frac{M_W}{M_{W,CC}}\right)^{\alpha_{PE}} - 1\right], \qquad \text{(EQN 13)}$$

wherein [η] is the measured intrinsic viscosity, $[\eta]_{cc}$ is the intrinsic viscosity from the conventional calibration (or cony GPC), Mw is the measured weight average molecular weight, and $M_{w,cc}$ is the weight average molecular weight of the conventional calibration. The weight average molecular weight by light scattering (LS) is commonly referred to as "absolute weight average molecular weight" or "Mw(abs)." The $M_{w,cc}$ from using conventional GPC molecular weight calibration curve ("conventional calibration") is often referred to as "polymer chain backbone molecular weight," "conventional weight average molecular weight" and "Mw (conv)."

All statistical values with the "cc or cony" subscript are determined using their respective elution volumes, the corresponding conventional calibration as previously described, and the concentration (Ci). The non-subscripted values are measured values based on the mass detector, LALLS, and viscometer areas. The value of $K_{PE}$ is adjusted iteratively, until the linear reference sample has a gpeBR measured value of zero. For example, the final values for a and Log K for the determination of gpcBR in this particular case are 0.725 and −3.355, respectively, for polyethylene, and 0.722 and −3.993, respectively, for polystyrene.

Once the K and a values have been determined using the procedure discussed previously, the procedure was repeated using the branched samples. The branched samples were analyzed using the final Mark-Houwink constants as the best "cc" calibration values.

The interpretation of gpcBR is straight forward. For linear polymers, gpcBR will be close to zero, since the values measured by LS and viscometry will be close to the conventional calibration standard. For branched polymers, gpcBR will be higher than zero, especially with high levels of long chain branching, because the measured polymer molecular weight will be higher than the calculated $M_{w,cc}$ and the calculated $IV_{cc}$ will be higher than the measured polymer IV. In fact, the gpcBR value represents the fractional IV change due to the molecular size contraction effect as a result of polymer branching. A gpcBR value of 0.5 or 2.0 would mean a molecular size contraction effect of IV at the level of 50% and 200%, respectively, versus a linear polymer molecule of equivalent weight.

For these particular examples, the advantage of using gpcBR, in comparison to a traditional "g' index" and branching frequency calculations, is due to the higher precision of gpcBR. All of the parameters used in the gpcBR index determination are obtained with good precision, and are not detrimentally affected by the low TDGPC detector response at high molecular weight from the concentration detector. Errors in detector volume alignment also do not affect the precision of the gpcBR index determination.

Calculation of LCB Frequency

The $LCB_f$ was calculated for each polymer sample by the following procedure: 1). The light scattering, viscosity, and concentration detectors were calibrated with NBS 1475 homopolymer polyethylene (or equivalent reference); 2) The light scattering and viscometer detector offsets were corrected relative to the concentration detector as described above in the calibration section (see references to Mourey and Balke); 3) Baselines were subtracted from the light scattering, viscometer, and concentration chromatograms and set integration windows making certain to integrate all of the low molecular weight retention volume range in the light scattering chromatogram that is observable from the refractometer chromatogram; 4) A linear homopolymer polyethylene Mark-Houwink reference line was established by injecting a standard with a polydispersity of at least 3.0, calculate the data file (from above calibration method), and record the intrinsic viscosity and molecular weight from the mass constant corrected data for each chromatographic slice; 5) The sample of interest was analyzed, the data file (from above calibration method) was calculated, and the intrinsic viscosity and molecular weight from the mass constant, corrected data for each chromatographic slice, were recorded. At lower molecular weights, the intrinsic viscosity and the molecular weight data may need to be extrapolated such that the measured molecular weight and intrinsic viscosity asymptotically approach a linear homopolymer GPC calibration curve; 6) The homopolymer linear reference intrinsic viscosity was shifted at each point (i) by the following factor: IVi=IVi*0.964 where IV is the intrinsic viscosity; 7) The homopolymer linear reference molecular weight was shifted by the following factor: M=M*1.037 where M is the molecular weight; 8) The g' at each chromatographic slice was calculated according to the following equation: g'=(IV(LDPE)/IV(linear reference)), at the same M.

The IV (linear reference) was calculated from a fifth-order polynomial fit of the reference Mark-Houwink Plot and where IV(linear reference) is the intrinsic viscosity of the linear homopolymer polyethylene reference (adding an amount of SCB (short chain branching) to account for backbiting through 6) and 7) at the same molecular weight (M)). The IV ratio is assumed to be one at molecular weights less than 3,500 g/mol to account for natural scatter in the light scattering data. 9) The number of branches at each data slice was calculated according to the following equation:

$$\left[\frac{IV_{LDPE}}{IV_{linear\_reference}}\right]_M^{1.33} = \left[\left(1+\frac{B_n}{7}\right)^{1/2} + \frac{4}{9}\frac{B_n}{\pi}\right]^{-1/2}. \quad (10)$$

The average LCB quantity was calculated across all of the slices (i), according to the following equation (EQN. L):

$$LCB_{1000C} = \frac{\sum_{M=3500}^{i}\left(\frac{B_{n_i}}{14000}c_i\right)}{\Sigma c_i}. \quad \text{(EQN. L)}$$

Nuclear Magnetic Resonance ($^{13}C$ NMR)

Samples were prepared by adding approximately "3 g" of a "50/50 mixture of tetrachloroethane-d2/orthodichlorobenzene, containing 0.025 M Cr(AcAc)$_3$," to a "0.25 to 0.40 g" polymer sample, in a 10 mm NMR tube. Oxygen was removed from the sample by purging the tube headspace with nitrogen. The samples were dissolved and homogenized by heating the tube and its contents to 145-150° C. using a heating block and heat gun. Each sample was visually inspected to ensure homogeneity.

All data were collected using a Bruker 400 MHz spectrometer. The data was acquired using a six second pulse repetition delay, 90-degree flip angles, and inverse gated decoupling, with a sample temperature of 120° C. All measurements were made on non-spinning samples in locked mode. Samples were allowed to thermally equilibrate for seven minutes prior to data acquisition. The 13C NMR chemical shifts were internally referenced to the EEE triad at 30.0 ppm. The "C6+" value is a direct measure of C6+ branches in LDPE, where the long branches are not distinguished from "chain ends." The "32.2 ppm" peak, representing the third carbon from the end of all chains or branches of six or more carbons, is used to determine the "C6+" value.

The amyl group content of the ethylene-based polymer is determined by 13C NMR.

Differential scanning calorimetry (DSC) for measuring the decomposition temperature is performed on a TA instruments Q200 calorimeter at a ramp rate of 10° C. from 0 to 400° C. under a nitrogen atmosphere with a sample size of 7 to 10 milligrams (mg).

The amyl group content of the ethylene-based polymer is determined by 13C NMR.

Crystallization Elution Fractionation (CEF) Method

The Crystallization Elution Fractionation (CEF) technology is conducted according to Monrabal et al, Macromol. Symp. 257, 71-79 (2007). The CEF instrument is equipped with an IR-4 or IR-5 detector (such as that sold commercially from PolymerChar, Spain) and a two angle light scattering detector Model 2040 (such as those sold commercially from Precision Detectors). A 10 micron guard column of 50 mm×4.6 mm (such as that sold commercially from PolymerLabs) is installed before the IR-4 or IR-5 detector in the detector oven. Ortho-dichlorobenzene (ODCB, 99% anhydrous grade) and 2,5-di-tert-butyl-4-methylphenol (BHT) (such as commercially available from Sigma-Aldrich) are obtained. Silica gel 40 (particle size 0.2-0.5 mm) (such as commercially available from EMD Chemicals) is also obtained. The silica gel is dried in a vacuum oven at 160° C. for at least two hours before use. ODCB is sparged with dried nitrogen ($N_2$) for one hour before use. Dried nitrogen is obtained by passing nitrogen at <90 psig over $CaCO_3$ and 5 Å molecular sieves. ODCB is further dried by adding five grams of the dried silica to two liters of ODCB or by pumping through a column or columns packed with dried silica between 0.1 mL/min to 1.0 ml/min. Eight hundred milligrams of BHT are added to two liters of ODCB if no inert gas such as $N_2$ is used in purging the sample vial. Dried ODCB with or without BHT is hereinafter referred to as "ODCB-m." A sample solution is prepared by, using the autosampler, dissolving a polymer sample in ODCB-m at 4 mg/ml under shaking at 160° C. for 2 hours. 300 μL of the sample solution is injected into the column. The temperature profile of CEF is: crystallization at 3° C./min from 110° C. to 30° C., thermal equilibrium at 30° C. for 5 minutes (including Soluble Fraction Elution Time being set as 2 minutes), and elution at 3° C./min from 30° C. to 140° C. The flow rate during crystallization is 0.052 mL/min. The flow rate during elution is 0.50 mL/min. The IR-4 or IR-5 signal data is collected at one data point/second.

The CEF column is packed with glass beads at 125 μm±6% (such as those commercially available with acid wash from MO-SCI Specialty Products) with ⅛ inch stainless tubing according to U.S. Pat. No. 8,372,931. The internal liquid volume of the CEF column is between 2.1 mL and 2.3 mL. Temperature calibration is performed by using a mixture of NIST Standard Reference Material linear polyethylene 1475a (1.0 mg/ml) and EICOSANE (2 mg/ml) in ODCB-m. The calibration consists of four steps: (1) calculating the delay volume defined as the temperature offset between the measured peak elution temperature of EICOSANE minus 30.00° C.; (2) subtracting the temperature offset of the elution temperature from the CEF raw temperature data. It is noted that this temperature offset is a function of experimental conditions, such as elution temperature, elution flow rate, etc.; (3) creating a linear calibration line transforming the elution temperature across a range of 30.00° C. and 140.00° C. such that NIST linear polyethylene 1475a has a peak temperature at 101.00° C., and EICOSANE has a peak temperature of 30.00° C., (4) for the soluble fraction measured isothermally at 30° C., the elution temperature is extrapolated linearly by using the elution heating rate of 3° C./min. The reported elution peak temperatures are obtained such that the observed comonomer content calibration curve agrees with those previously reported in U.S. Pat. No. 8,372,931.

Carbonyl Ratio

The carbonyl ratio was determined by Fourier Transform Infrared Spectroscopy (FTIR). Films of 10-15 mils thickness are pressed in a 15 mil steel shim between two sheets of TEFLON™ polymer by heating on high pressure (40,000 psi) at 190° C. for 30 seconds and then quench-cooled on high pressure (40,000 psi) at 15° C. for 30 seconds. FTIR spectra are collected using the following instrument and parameters: Spectrometer: Thermo Nicolet Nexus 470; Software: OMNIC 8.3.103; Mode: Transmission; Source: IR; Detector: DTGS KBr; Number of sample scans: 64;Resolution: 4 cm. The relative level of carbonyl groups are found by the ratio of the absorbances at 1722 cm$^{-1}$ to absorbance at 2019 cm$^{-1}$ (internal polyethylene (PE) thickness).

Neutron Activation Method for Metals

Two sets of duplicate samples are prepared by transferring approximately 3.5 grams of polymer sample (for example, pellets) into pre-cleaned 2 dram polyethylene vials. Standards are prepared for each metal tested from their NIST traceable standard solutions (Certi. pure from SPEX) into 2-dram polyethylene vials. They are diluted using milli-Q pure water to 6ml and the vials are heat-sealed. The samples and standards are then analyzed for these elements, using a Mark I TRIGA nuclear reactor. The reactions and experimental conditions used for these elements are summarized in the Table A below. The samples are transferred to un-irradiated vials before doing the gamma-spectroscopy. The elemental concentrations are calculated using CANBERRA software and standard comparative technique. ND means Not Detected at the quoted detection limit of the NAA measurement system. Table A provides measurement parameters for Al determination. Other techniques, known in the art, such as mass balance, can be used to determine the metal content (e.g., Al) in a polymer composition.

TABLE 1

Initiator Efficiency

| Initiator | Reactor Temperature (° C.) | Initiator Efficiency (g PE/mol initiator) |
|---|---|---|
| DEDPH | 274 | 608,193 |
|  | 260 | 620,983 |
|  | 242 | 671,932 |
|  | 223 | 748,249 |
|  | 202 | 768,714 |
| DTBP | 276 | 646,730 |
|  | 262 | 726,631 |
|  | 243 | 761,618 |
|  | 221 | 869,760 |

As can be seen the DEDPH initiator is capable of producing low density polyethylene over the same temperature range and at the same initiator efficiency as the commercial peroxide initiator DTBP.

Poisoning of Molecular Catalysts with Initiators

A simple test is devised to study the poisoning effect of peroxides and carbon based initiators on molecular catalysts. For this study the carbon based initiator used is DEDPH and the peroxide initiator used is TRIGONOX™ 101 sold by Akzo-Nobel. In a 40 ml vial inside an oxygen and moisture free glovebox, 10 ml of 1-octene is added along with a free radical initiator. Subsequently 2 µmol of modified methaluminoxane, 0.12 µmol of an anilium borate cocatalyst and 0.12 µmol of a molecular catalyst (CAT A) are added. This catalyst combination begins polymerizing the octene result-

TABLE A

Reactions and experimental conditions used for elements during the NAA for Al

| Element | Nuclear reaction | Isotope | Half life | Reactor Power | Irradiation Time | Waiting Time | Counting Time | Gamma Energy, keV |
|---|---|---|---|---|---|---|---|---|
| Al | $^{27}$Al(n, γ)$^{28}$Al | $^{28}$Al | 2.24 m | 250 kW | 2 m | 4 m | 4.5 min | 1778.5 |

Differential scanning calorimetry (DSC) to determine the decomposition temp. is performed on a TA instruments Q200 calorimeter at a ramp rate of 10 C from 0 to 400 C.

The dissipation factor is the lost energy of an applied electrical field due to internal motion of a material placed in the field. The dissipation factor is measured on 50 mil plaques at a frequency of 2.47 GHz using Agilent 8753 ES S-parameter network analyzer with compatible split post dielectric resonator. The following parameters are used in compression molding of the plaques: 5 minutes at low pressure (500 psi) and 120° C., 5 minutes at high pressure (2500 psi) and 120° C., and Water cooling to room temperature.

Experimental

Equivalency of C—C Initiators to Traditional Peroxides

In order to show that carbon based initiators can polymerize ethylene in the same manner as normal peroxides, an ethylene polymerization reaction is carried out under the following conditions: Pressure—28,000 psi, Temperature—200-280° C., Ethylene Feed rate—12 lb/hr, Reactor Size—300 ml.

Two different initiators are evaluated, a typical peroxide initiator di-tertbutyl peroxide (DTBP) and a carbon based initiator diethyldiphenylhexane (DEDPH). At each temp., the conversion of ethylene per mole initiator is determined, and shown in Table 1.

ing in a measureable temperature rise which is directly related to the amount of polymer formed. The results are shown in Table 2. As the level of the peroxide is increased, the efficiency of the molecular catalyst decreases as indicated by a reduced temperature rise. In the case of the carbon based initiator, increasing the level of initiator does not affect the efficiency of the molecular catalyst.

TABLE 2

| Initiator added (µmol) | Temp rise measured (° C.) |
|---|---|
| TRIGONOX 101 (0) - baseline | 66 |
| TRIGONOX 101 (12.6) | 39 |
| TRIGONOX 101 (25.2) | 8.6 |
| DEDPH (0) - baseline | 64 |
| DEDPH (14.1) | 62 |
| DEDPH (28.2) | 59 |

Representative Polymerization—Two Separate Reaction Zones

A high pressure "300 ml" continuous autoclave reactor is separated into two equal zones with a baffle, pressurized with ethylene to 28,000 psi, at an ethylene flow rate of 15 lb/hr. Propylene is added into the ethylene stream at 3 mol %, based on the total amount of ethylene added to the polymerization process. The resulting mixture is heated to 195° C.

To the reactor modified methylaluminoxane (MMAO) cocatalyst and the catalyst (CAT A) are added to the first zone, to produce concentrations in the reactor equal to 8.2 mol ppm Al and 0.016 mol ppm Zr; each "ppm" (parts per million) is based on the total amount of ethylene added to the polymerization process. The catalyst (CAT A) is zirconium, dimethyl [(2,2'-[1,3 propanediylbis(oxy-kO)]bis[3",5,5"-tris(1,1-dimethylethyl)-5'-methyl-[1,1',3',1"-terphenyl]-2'-olato-kO]](2-)]-, (OC-6-33)-) (see WO 2007/136494 (Cat. A11), fully incorporated herein by reference).

The first ethylene-based polymer from the first reactor zone is transferred to the second reactor zone, along with ethylene. The C—C initiator is added to the second reactor zone to produce a concentration of the C—C initiator in the second zone of 2.1 mol ppm, based on the total amount of ethylene added to the polymerization process. An ethylene-based polymer composition is typically produced at 0.78 lb/h (density=0.9296 g/cc, melt index (MI or I2)=1.12 dg/min).

Representative Polymerization—One Reaction Zone

A high pressure "300 ml" continuous autoclave reactor is pressured with ethylene to 28,000 psi, at an ethylene flow rate of 12 lb/h (pounds per hour). Propylene is added at 1 mol % (mole percent), based on the total amount of ethylene added to the polymerization process, into the ethylene stream. This mixture is heated to 220° C. The C—C initiator is added to produce a concentration in the reactor of 1.5 mol ppm, based on the total amount of ethylene added to the polymerization process. To the reactor, MMAO cocatalyst and CAT A are added to produce concentrations in the reactor equal to 16.8 mol ppm Al and 0.071 mol ppm Zr; each "ppm" is based on the total amount of ethylene added to the polymerization process. A polyethylene composition is produced at 0.72 lb/hr of polyethylene (density=0.9275 g/cc, melt index (MI or I2)=1.92 dg/min).

Polymerization—One Reaction Zone

A high pressure "300 ml" continuous autoclave reactor is pressured with ethylene to 28,000 psi, at an ethylene flow rate of 17 lb/h (pounds per hour). Propylene is added at 0.8-1 mol % (mole percent), based on the total amount of ethylene added to the polymerization process, into the ethylene stream. This mixture is heated to 220° C. Then 3,4-diethyl-3,4-diphenyl hexane (Structure IV) is added to produce a concentration in the reactor of 1.86 mol ppm, based on the total amount of ethylene added to the polymerization process. To the reactor, MMAO cocatalyst and CAT A are added to produce concentrations in the reactor equal to 5.35 mol ppm Al and 0.08 mol ppm Zr; each "ppm" is based on the total amount of ethylene added to the polymerization process. The average reactor temperature and propylene concentration used to produce the Examples and Comparative Example 1 (LDPE only) is shown in Table 3. The process used to form Comparative Example 1 was the same as described above, except no CAT A and no MMAO were added to the polymerization.

Melt Index, Density, and Carbonyl Ratio of Examples and Comparative Example

The melt index, density, and carbonyl ratio for the Examples and Comparative Example are shown in Table 3. The Examples spanned a melt index range of 5.29-12.35 and also exhibited high densities ranging from 0.9264-0.9310 g/cc, much higher than that of Comparative Example 1 at 0.9186 g/cc. The carbonyl ratios measured for these examples are extremely low as no carbonyl containing compounds are added to the reactor, unlike typical commercial LDPE samples produced with traditional initiators which decompose to carbonyl containing products.

TABLE 3

| Ex. | Average Reactor Temperature (° C.) | Propylene concentration (mol %) | Melt Index (I2) (dg/min) | Density (g/cc) | Carbonyl Ratio |
|---|---|---|---|---|---|
| 1 | 242 | 1.0 | 5.29 | 0.9304 | 0.0037 |
| 2 | 234 | 1.0 | 7.63 | 0.9310 | 0.0113 |
| 3 | 227 | 0.8 | 12.35 | 0.9264 | 0.0075 |
| 4 | 226 | 0.8 | 11.50 | 0.9297 | 0.0045 |
| CE 1 | 231 | 3.0 | 6.82 | 0.9186 | 0.0044 |
| LDPE 722* | | | | | 0.10 |

*Available from The Dow Chemical Company, and prepared using a peroxide as initiator.

Figure 1:
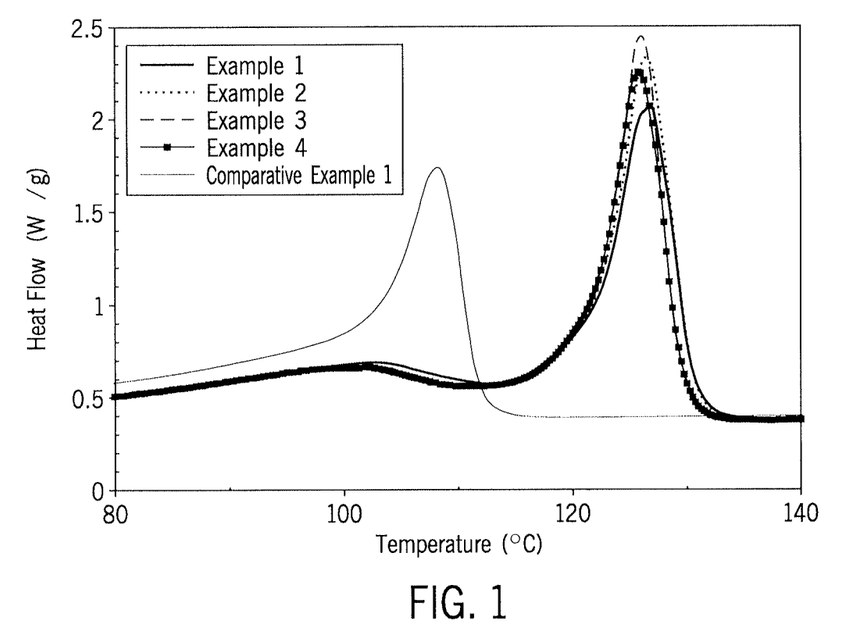
FIG. 1 depicts "DSC heat flow vs. temperature" of Examples 1-4 and Comparative Example 1.
Figure 2:
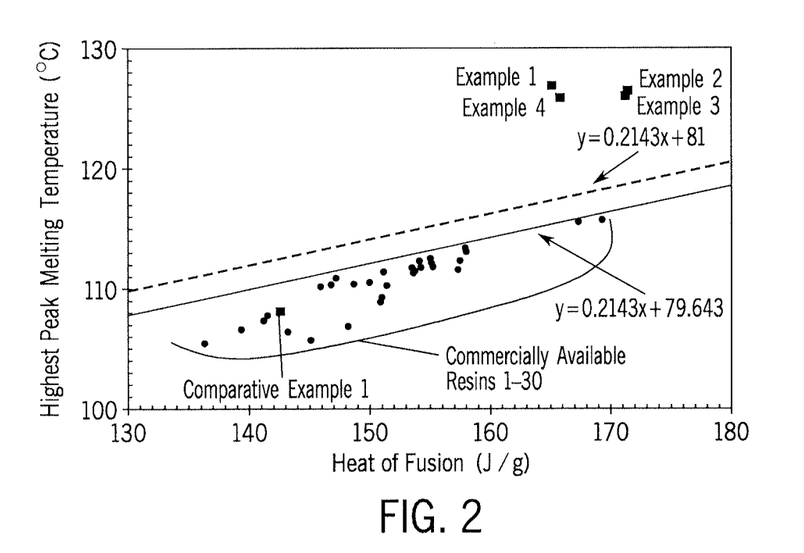
FIG. 2 depicts "Highest peak melting temperature vs. heat of fusion" from DSC of Examples 1-4 and Comparative Example 1 and commercially available LDPE resins 1-30 and claim lines from WO 2009/114661.

The DSC results for the Examples and Comparative Example are shown in Table 4 and in FIG. 1. FIG. 2 shows a plot of the "highest peak melting temperature versus the heat of fusion" for Examples 1-4 and CE1, in which the Example numbers are shown in the figure, as compared to commercially available LDPE results from WO 2009/114661.

TABLE 4

| Ex. | $T_{m1}$ (° C.) | $T_{m2}$ (° C.) | Heat of Fusion (J/g) | % Cryst. | $T_{c1}$ (° C.) | $T_{c2}$ (° C.) | $T_{c3}$ (° C.) |
|---|---|---|---|---|---|---|---|
| 1 | 126.9 | 102.9 | 165.1 | 56.5 | 111.6 | 94.4 | 61.6 |
| 2 | 126.5 | 101.7 | 171.4 | 58.7 | 112.2 | 93.3 | NA |
| 3 | 126.0 | 101.0 | 171.2 | 58.6 | 112.5 | 92.7 | NA |
| 4 | 125.9 | 101.5 | 165.8 | 56.8 | 112.2 | 92.9 | NA |
| CE 1 | 108.1 | NA | 142.6 | 48.8 | 94.1 | 58.4 | NA |

TDGPC (Triple Detector GPC or 3D-GPC) of Examples and Comparative Example

Examples 1-4 and Comparative Example 1 were analyzed by the TDGPC technique as described above with results in Table 5. The Examples as compared to Comparative Example 1 show a lower Mw, Mz, and Mw, and Mw/Mn, and Mw (abs)/Mw (Cony). Also, the measures of long chain branching shown, LCBf and gpcBR, are lower for the Examples as compared to Comparative Example 1.

TABLE 5

| | Mn, Conv. (g/mol) | Mw, Conv. (g/mol) | Mz, Conv. (g/mol) | Mw/Mn, Conv. | Mw, Abs (g/mol) | Mz, Abs (g/mol) | Mw (Abs)/ Mw(Conv) | LCBf | gpcBR |
|---|---|---|---|---|---|---|---|---|---|
| Ex. 1 | 15,092 | 65,462 | 218,163 | 4.34 | 104,777 | 2,766,618 | 1.60 | 0.29 | 0.93 |
| Ex. 2 | 13,900 | 60,166 | 188,245 | 4.33 | 87,884 | 2,436,140 | 1.46 | 0.19 | 0.75 |
| Ex. 3 | 12,918 | 55,955 | 184,159 | 4.33 | 84,600 | 2,537,916 | 1.51 | 0.28 | 0.80 |
| Ex. 4 | 12,764 | 56,704 | 191,507 | 4.44 | 86,066 | 2,559,198 | 1.52 | 0.27 | 0.84 |
| CE 1 | 14,702 | 197,178 | 905,894 | 13.41 | 1,092,195 | 8,551,792 | 5.54 | 4.06 | 8.45 |

CEF of Examples

Figure 3:
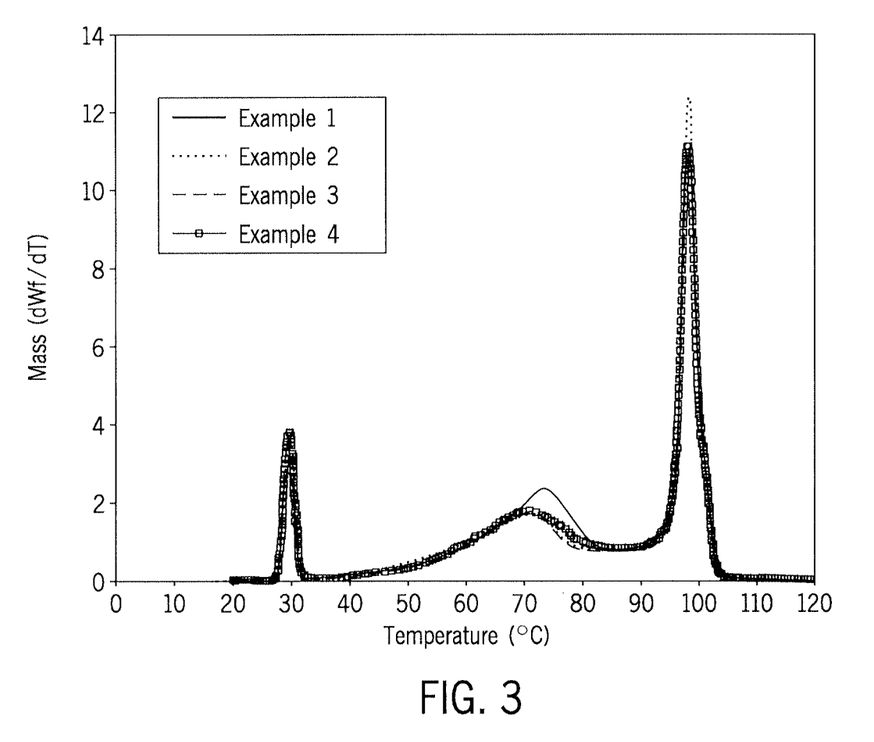
FIG. 3 depicts CEF mass vs. temperature of Examples 1-4 and Comparative Example 1.

The CEF of the Examples are summarized in Table 6 and FIG. 3. The examples contained three fractions. For the Examples the highest temperature fraction was greater than 98° C. indicative of the HDPE fraction coupled with LCB as seen in the TDGPC.

TABLE 6

|  | Temp Range of Each Zone (° C.) | | | Peak Temp of Each Zone (° C.) | | | wt % of Each zone | | |
| --- | --- | --- | --- | --- | --- | --- | --- | --- | --- |
|  | Zone 1 | Zone 2 | Zone 3 | Zone 1 | Zone 2 | Zone 3 | Zone 1 | Zone 2 | Zone 3 |
| Ex. 1 | 25.04 to 34.48 | 34.58 to 88.32 | 88.41 to 119.96 | 29.66 | 73.46 | 98.50 | 6.44 | 46.18 | 47.38 |
| Ex. 2 | 25.03 to 34.48 | 34.58 to 83.23 | 83.32 to 120.00 | 29.66 | 70.92 | 98.51 | 7.87 | 35.84 | 56.30 |
| Ex. 3 | 25.03 to 34.46 | 34.55 to 83.03 | 83.13 to 119.96 | 29.76 | 70.21 | 98.45 | 9.14 | 36.99 | 53.87 |
| Ex. 4 | 25.03 to 34.47 | 34.57 to 87.00 | 87.08 to 119.96 | 29.71 | 70.37 | 98.39 | 8.94 | 42.26 | 48.81 |

What is claimed is:

1. A process for making a composition comprising an ethylene-based polymer, the process comprising the steps of:
   (A) contacting under first polymerization conditions at least ethylene and at least one molecular catalyst to form a first ethylene-based polymer, the molecular catalyst is a metal complex of a polyvalent aryloxyether corresponding to Structure B:

(Structure B)

where $M^3$ is Hf or Zr;

$Ar^4$ independently at each occurrence is a substituted $C_{9-20}$ aryl group, wherein the substituents, independently at each occurrence, are selected from the group consisting of alkyl; cycloalkyl; and aryl groups; and halo-, trihydrocarbylsilyl- and halohydrocarbyl-substituted derivatives thereof, with the proviso that at least one substituent lacks co-planarity with the aryl group to which it is attached;

$T^4$ is a $C_{2-20}$ alkylene, cycloalkylene or cycloalkenylene group, or an inertly substituted derivative thereof;

$R^{21}$ independently at each occurrence is hydrogen, halo, hydrocarbyl, trihydrocarbylsilyl, trihydrocarbylsilylhydrocarbyl, alkoxy or di(hydrocarbyl)amino group of up to 50 atoms not counting hydrogen;

$R^3$ independently at each occurrence is hydrogen, halo, hydrocarbyl, trihydrocarbylsilyl, trihydrocarbylsilylhydrocarbyl, alkoxy or amino of up to 50 atoms not counting hydrogen, or two $R^3$ groups on the same arylene ring together or an $R^3$ and an $R^{21}$ group on the same or different arylene ring together form a divalent ligand group attached to the arylene group in two positions or join two different arylene rings together; and $R^D$, independently at each occurrence is halo or a hydrocarbyl or trihydrocarbylsilyl group of up to 20 atoms not counting hydrogen, or 2 RD groups together are a hydrocarbylene, hydrocarbadiyl, diene, or poly(hydrocarbyl)silylene group, and (B) contacting under second polymerization conditions the first ethylene-based polymer of (A) with at least additional ethylene and a carbon-carbon free radical initiator of Structure I:

(Structure I)

wherein $R_1$, $R_2$, $R_3$, $R_4$, $R_5$ and $R_6$ are each, independently, hydrogen or a hydrocarbyl group and wherein, optionally, two or more R groups ($R_1$, $R_2$, $R_3$, $R_4$, $R_5$ and $R_6$) form a ring structure, with the proviso that at least one of $R_2$ and $R_5$, and at least one of $R_3$ and $R_6$ is a hydrocarbyl group of at least two carbon atoms, to form a polymer composition comprising a second ethylene-based polymer.

2. The process of claim 1, in which the process takes place in one reaction zone.

3. The process of claim 1, in which the process takes place in at least two reaction zones.

4. The process of claim 1 in which the carbon-carbon free radical initiator is of Structure II:

(Structure II)

5. The process of claim 1 in which the first polymerization conditions include a pressure of at least 14,000 pounds per square inch (psi) and a temperature of at least 195° C.

6. The process of claim 1 in which hydrogen gas is not introduced into either step (A) or (B).

7. A process for making a composition comprising an ethylene-based polymer, the process comprising the steps of:
   (A) contacting under first polymerization conditions at least ethylene and at least one molecular catalyst to form a first ethylene-based polymer, and (B) contacting under second polymerization conditions the first ethylene-based polymer of (A) with at least additional ethylene and a carbon-carbon free radical initiator of Structure I:

(Structure I)

wherein $R_1$, $R_2$, $R_3$, $R_4$, $R_5$ and $R_6$ are each, independently, hydrogen or a hydrocarbyl group and wherein, optionally, two or more R groups ($R_1$, $R_2$, $R_3$, $R_4$, $R_5$ and $R_6$) form a ring structure, with the proviso that at least one of $R_2$ and $R_5$, and at least one of $R_3$ and $R_6$ is a hydrocarbyl group of at least two carbon atoms, to form a polymer composition comprising a second ethylene-based polymer, wherein the first polymerization conditions include a pressure of at least 14,000 pounds per square inch (psi) and a temperature of at least 195° C.

8. The process of claim 7, in which the process takes place in one reaction zone.

9. The process of claim 7, in which the process takes place in at least two reaction zones.

10. The process of claim 7 in which the molecular catalyst is a metal complex of a polyvalent aryloxyether corresponding to Structure B:

(Structure B)

where $M^3$ is Hf or Zr;

$Ar^4$ independently at each occurrence is a substituted $C_{9-20}$ aryl group, wherein the substituents, independently at each occurrence, are selected from the group consisting of alkyl; cycloalkyl; and aryl groups; and halo-, trihydrocarbylsilyl- and halohydrocarbyl-substituted derivatives thereof, with the proviso that at least one substituent lacks co-planarity with the aryl group to which it is attached;

$T^4$ is a C2-20 alkylene, cycloalkylene or cycloalkenylene group, or an inertly substituted derivative thereof;

$R^{21}$ independently at each occurrence is hydrogen, halo, hydrocarbyl, trihydrocarbylsilyl, trihydrocarbylsilylhydrocarbyl, alkoxy or di(hydrocarbyl)amino group of up to 50 atoms not counting hydrogen;

$R^3$ independently at each occurrence is hydrogen, halo, hydrocarbyl, trihydrocarbylsilyl, trihydrocarbylsilylhydrocarbyl, alkoxy or amino of up to 50 atoms not counting hydrogen, or two $R^3$ groups on the same arylene ring together or an $R^3$ and an $R^{21}$ group on the same or different arylene ring together form a divalent ligand group attached to the arylene group in two positions or join two different arylene rings together; and $R^D$, independently at each occurrence is halo or a hydrocarbyl or trihydrocarbylsilyl group of up to 20 atoms not counting hydrogen, or 2 RD groups together are a hydrocarbylene, hydrocarbadiyl, diene, or poly(hydrocarbyl)silylene group.

11. The process of claim 7 in which the carbon-carbon free radical initiator is of Structure II:

(Structure II)

12. The process of claim 7 in which hydrogen gas is not introduced into either step (A) or (B).

* * * * *